US 6,563,013 B1

(12) United States Patent
Murota

(10) Patent No.: US 6,563,013 B1
(45) Date of Patent: May 13, 2003

(54) ABSORBENT ARTICLE HAVING CHANNEL

(75) Inventor: Tsutomu Murota, Himeji (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/856,016

(22) PCT Filed: Nov. 26, 1999

(86) PCT No.: PCT/IB99/01897

§ 371 (c)(1),
(2), (4) Date: Jul. 23, 2001

(87) PCT Pub. No.: WO00/32145

PCT Pub. Date: Jun. 8, 2000

(30) Foreign Application Priority Data

Nov. 30, 1998 (WO) .................. PCT/US98/25326
Nov. 30, 1998 (WO) .................. PCT/US98/25327

(51) Int. Cl.⁷ ............................................. A61F 13/15
(52) U.S. Cl. ................... 604/380; 604/385.01; 604/379
(58) Field of Search ................... 604/380, 378, 604/379, 385.01, 383; 428/170, 171, 172

(56) References Cited

U.S. PATENT DOCUMENTS 3,403,681 A * 10/1968 Hoey et al. ................. 128/290
3,508,548 A * 4/1970 Hochstrasser et al. ....... 128/285
4,389,211 A * 6/1983 Lenaghan .................... 604/383
4,443,512 A * 4/1984 Delvaux ...................... 428/162
4,790,838 A   12/1988 Pigneul et al.
5,387,206 A * 2/1995 Valentine et al. ........... 604/358
H1511 H * 12/1995 Chappell et al. ............ 604/383
5,611,879 A   3/1997 Morman
5,925,026 A * 7/1999 Arteman et al. ............. 604/383
5,935,682 A * 8/1999 Wallstrom ................... 428/138
6,326,525 B1 * 12/2001 Hamajima et al. ........... 604/378

FOREIGN PATENT DOCUMENTS

EP  0 291 316 A2  11/1988
EP  0 769 284 B1  2/2002
GB  2 319 730 A   6/1998

* cited by examiner

Primary Examiner—Weilun Lo
Assistant Examiner—Jacqueline F Stephens
(74) Attorney, Agent, or Firm—Kevin C. Johnson

(57) ABSTRACT

An absorbent article having a channel is disclosed. The absorbent article comprises a liquid permeable topsheet, a liquid impermeable backsheet, and an absorbent core therebetween. The channel length is at least 10% of the length of the absorbent core. The channel has at least one first portion and at least one second portion being of different compression relative to one another. The first portion extends continuously along at least 30% of the length of the channel.

5 Claims, 15 Drawing Sheets

ABSORBENT ARTICLE HAVING CHANNEL

FIELD

This invention relates to an absorbent article, such as a sanitary napkin, a baby diaper, or an adult incontinence product, having a channel. More specifically, this invention relates to an absorbent article having a channel including at least one first portion and at lease one second portion being of different compression relative to one another.

BACKGROUND

Absorbent articles, such as sanitary napkins, baby diapers, adult incontinence products are well known. Such absorbent articles have a liquid permeable topsheet, a liquid impermeable backsheet, and an absorbent core therebetween. The absorbent article is designed to absorb body fluid, such as urine and menses into the absorbent core through the topsheet. One of the important functions of the absorbent article is to absorb and hold body fluid in the absorbent core and prevent from leaking of body fluid out of the absorbent core. Therefore, the absorbent core should have enough capacity to absorb and hold body fluid. However, the wearer sometimes experiences that the body fluid leaks out of the absorbent articles and soils the wearer's undergarment and/ or cloths. The leakage of body fluid tends to happen at the longitudinal sides of the absorbent article. The lateral width of the absorbent article is typically shorter than the longitudinal length. Therefore, body fluid reaches the longitudinal sides of the absorbent article earlier than the lateral edges. Body fluid does not always reach the longitudinal side of the absorbent article before changing the absorbent article. However, the wearer still feels insecure in the absorbent article with respect to leakage of body fluid if body fluid reaches near the longitudinal side.

In order for the absorbent article to absorb body fluid effectively without leakage of body fluid out of the absorbent article, the absorbent article also should be applied closely to the wearer's body such that the absorbent article can catch body fluid in an intended place of the absorbent article (e.g., the center of the absorbent core). For example, this can be achieved by rendering a portion of the absorbent core thick such that the absorbent core is closely disposed to the wearer's body. However, this gives the wearer a feeling of bulkiness.

In order to address to the issue of body fluid leakage from the absorbent article, absorbent articles having a channel have been provided. The channel is formed by compressing, e.g., the topsheet side toward the absorbent core. As a result of compression, the absorbent core and the topsheet deforms such that the channel is created. Body fluid running on the topsheet flows into the channel and tends to flow along the channel rather than continuing along the topsheet. In addition, because the absorbent core is compressed, and therefore has a high density area versus the rest area of the absorbent core, body fluid flowing into the channel tends to diffuse along the high density area. Further, the absorbent article preferentially bends at the channel. Therefore, disposing the compressed channel in an appropriate position, such as along opposite longitudinal sides of the absorbent article, improves the fit of the absorbent article to the wearer's body.

Attempts to improve a control of body fluid flow in the channel have been made. For example, there is an absorbent article having a pair of grooves being formed in a top surface of the napkin by compression-molding along longitudinal opposite sides of the napkin. Each of these grooves has lower and higher density compressed zones arranged on the bottom thereof alternatively and separately in a longitudinal direction thereof. The higher compressed zone has less height than the lower compressed zone on the bottom. Such a channel is disclosed, e.g., in JP Patent publication 97/108262-A published on Apr. 28, 1997. It is said that this structure serves to suppress a phenomenon that the quantity of body exudates once having flowed into the grooves might too rapidly spread longitudinally along the grooves and thereby prevent the longitudinal opposite side edges of the napkin as well as the wearer's undergarments contracted by these side edges from being stained with any quantity of body exudates. However, the bottom surface of the groove has an uneven geometry due to the higher compressed zone and lower compressed zone arranged alternately in a row. Therefore, body fluid cannot travel along the bottom surface of the groove so smoothly. This tends to result in too much suppressing of body fluid flow in the groove and the groove may not work as expected initially for fluid flow in the direction of the channel.

The structural integrity of the channel formed on the absorbent article also must be maintained as long as possible over a period of use of the absorbent article. The topsheet of the channel portion is typically joined to the absorbent core by applying heat, heat and pressure, and/or adhesive between the topsheet and the absorbent core. However, the topsheet of the channel portion sometimes detaches from the absorbent core due to, e.g., peeling force added to the channel portion caused by twisting of the absorbent article. As a result, the channel loses its shape and does not work as initially expected.

Based on the foregoing, there is a need for an absorbent article having a channel, wherein the channel provides controlled, but smooth, body fluid flow in the channel. There is also a need for an absorbent article having a channel, wherein the structural integrity of the channel formed on the absorbent article is maintained as long as possible over a period of use of the absorbent article. None of the existing art provides all of the advantages and benefits of the present invention.

SUMMARY

The present invention provides an absorbent article having a channel. The absorbent article comprises a liquid permeable topsheet, a liquid impermeable backsheet, and an absorbent core therebetween. The channel length is at least 10% of the length of the absorbent core. The channel has at least one first portion and at least one second portion being of different compression relative to one another. The first portion extends continuously along at least 30% of the length of the channel.

The present invention also provides an absorbent article having a channel. The absorbent article comprises a liquid permeable topsheet, a liquid impermeable backsheet, and an absorbent core therebetween. The channel has at least one first portion and at least one second portion being of different compression relative to one another. At least two boundaries between the first and second portions are generally linear and generally non-parallel.

BRIEF DESCRIPTION OF THE DRAWINGS

While the specification concludes with claims which particularly point out and distinctly claim the invention, it is believed the present invention will be better understood from the following description of preferred embodiments taken in conjunction with the accompanying drawings, in which like reference numerals identify identical elements and wherein:

DETAILED DESCRIPTION OF THE INVENTION

Figure 1:
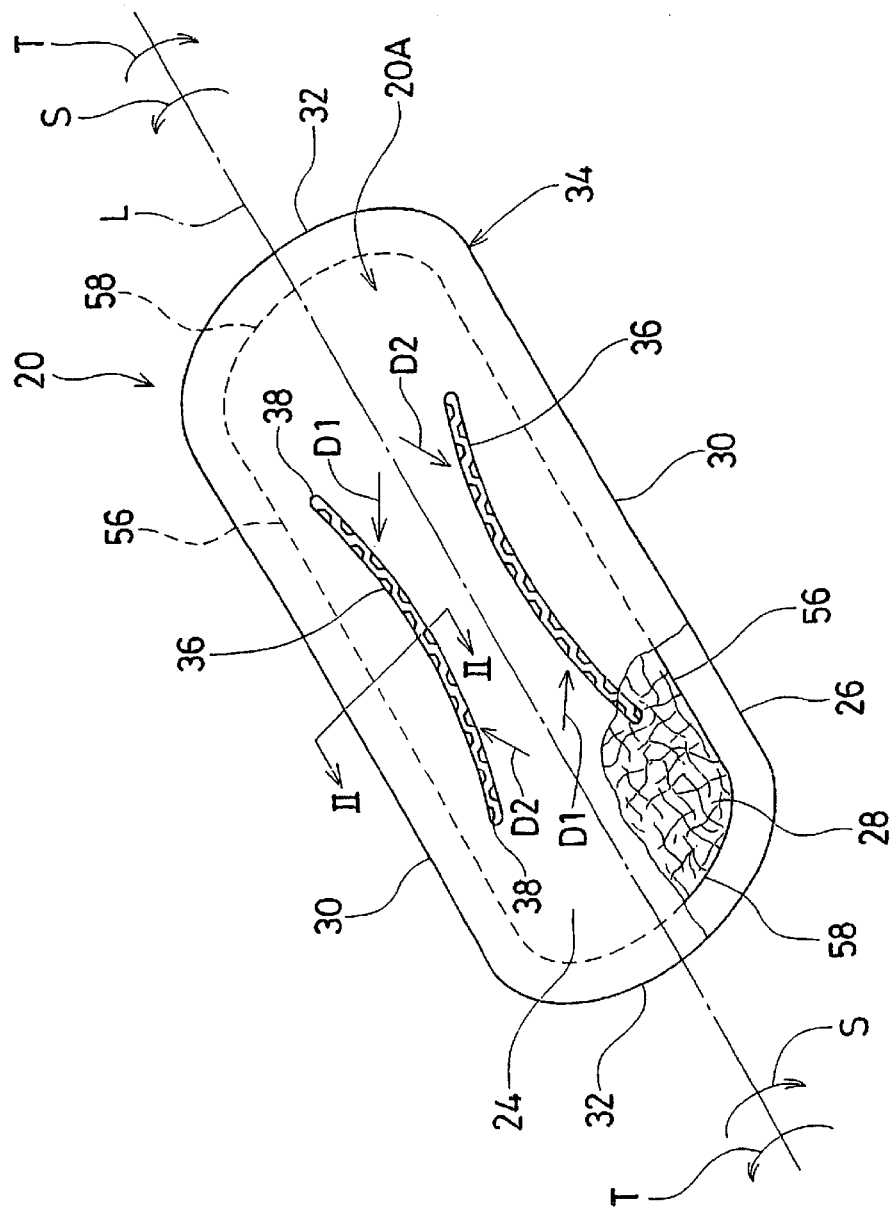
FIG. 1 is a perspective view of the absorbent article of the present invention with a portion of the structure being cut-away to more clearly show the construction of the absorbent article.

All cited references are incorporated herein by reference in their entireties. Citation of any reference is not an admission regarding any determination as to its availability as prior art to the claimed invention.

"Comprising" means that other steps and other elements which do not affect the end result can be added. This term encompasses the terms "consisting of" and "consisting essentially of".

Referring now to the drawings, the present invention is disclosed in a preferred but non-limiting embodiment.

FIG. 1 is a perspective view of the absorbent article, such as a sanitary napkin, 20 of the present invention with a portion of the structure being cut-away to more clearly show the construction of the sanitary napkin 20. The sanitary napkin 20 is used to collect vaginal discharges, such as menses, and prevent soiling of the wearer's clothing by such discharges. As shown in FIG. 1, the sanitary napkin 20 has two centerlines, a principal longitudinal centerline L and a principal transverse centerline (not shown in FIGS). Herein, "longitudinal" refers to a line, axis or direction in the plane of the sanitary napkin 20 that is generally aligned with (e.g. approximately parallel to) a vertical plane which bisects a standing wearer into left and right body halves when the sanitary napkin 20 is worn. Herein, "transverse" "lateral" or "width" are interchangeable, and refer to a line, axis or direction which lies within the plane of the sanitary napkin 20 that is generally perpendicular to the longitudinal direction. The sanitary napkin 20 also has two spaced apart longitudinal side edges 30, two spaced apart transverse or end edges (or "ends") 32, which together form the periphery 34 of the sanitary napkin 20.

The sanitary napkin 20 basically includes two surfaces, a liquid pervious body-contacting surface or "body surface" 20A that is intended to be worn adjacent to the body of the wearer, and a liquid impervious garment surface 20B (not shown in FIG. 1). The body surface 20A includes a liquid permeable topsheet 24 and the liquid impermeable garment surface 20B includes a liquid impermeable backsheet 26 which is joined to the topsheet 24. The sanitary napkin 20 includes an absorbent core 28 interposed between the topsheet 24 and the backsheet 26. The sanitary napkin 20 further includes channels 36 on the body surface 20A.

Figure 2:
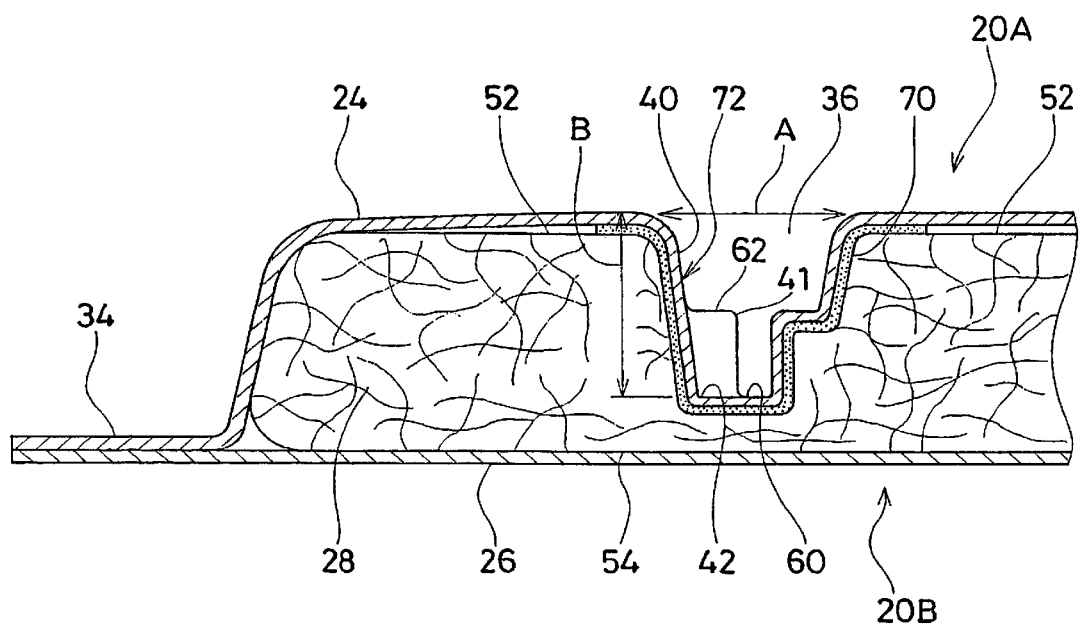
FIG. 2 is a fragmentary cross-sectional view of the absorbent article taken, along the line II—II of FIG. 1.

FIG. 2 shows the individual components of the sanitary napkin 20. The sanitary napkin 20 has at least three primary components, the topsheet 24, the backsheet 26, and the absorbent core 28 interposed therebetween. The topsheet 24, the backsheet 26, and the absorbent core 28 may be assembled in a variety of configurations known in the art (including layered or "sandwich" configurations and wrapped or "tube" configurations). FIG. 2 shows a preferred embodiment of the sanitary napkin 20 assembled in a sandwich construction in which the topsheet 24 and the backsheet 26 have length and width dimensions generally larger than those of the absorbent core 28. The topsheet 24 and the backsheet 26 extend beyond the edges of the absorbent core 28 to form portions of the periphery 34. The topsheet 24 is preferably joined to the body-facing side of the absorbent core 28 and the backsheet 26 is preferably joined to the garment-facing side of the absorbent core 28. The topsheet 24 and backsheet 26 can be joined to the absorbent core 28 in any suitable manner known in the art for this purpose, such as by an open pattern of adhesives. The portions of the topsheet 24 and backsheet 26 that extend beyond the edges of the absorbent core 28 are preferably also joined to each other. These portions of the topsheet 24 and backsheet 26 can also be joined in any suitable manner known in the art. Preferably, in the embodiment shown, these portions of the topsheet 24 and backsheet 26 are joined using adhesives over substantially the entire portions that extend beyond the edges of the absorbent core 28, and a crimp seal around the periphery 34 of the sanitary napkin 20 where the topsheet 24 and backsheet 26 are densified by the application of pressure or heat and pressure. Alternatively, the portions of the topsheet 24 and backsheet 26 may be joined using heat bonds, pressure bonds, ultrasonic bonds, dynamic mechanical bonds, or any other suitable attachment means or combinations of these attachment means as are known in the art.

The absorbent core 28 may be any absorbent means which is capable of absorbing or retaining liquids such as vaginal fluids (e.g., menses) and other certain body discharges. The absorbent core 28 has a garment surface 52 and a body surface 54 as shown in FIG. 2. The absorbent core 28 also has core side edges 56 and core end edges 58 as shown in FIG. 1. The absorbent core 28 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding, meltblown polymers including coform, cross-linked chemically modified cellulosic fibers, synthetic fibers, tissue including tissue wraps and tissue laminates, absorbent foams, absorbent sponges, superabsorbent polymers, absorbent gelling materials, or any equivalent material or combinations of materials, or mixtures of these. The configuration and construction of the absorbent core may also be varied (e.g., the absorbent core may have varying caliper zones, hydrophilic gradients, superabsorbent gradients, or lower density and lower average basis weight acquisition zones; or may comprise one or more layers or structures). The total absorbent capacity of the absorbent core should, however, be compatible with the design loading and the intended use of the sanitary napkin. Further, the size and absorbent capacity of the absorbent core may be varied to accommodate different uses such as incontinent pads, pantiliners, regular sanitary napkins, overnight sanitary napkins, or diapers.

An exemplary absorbent structure for use as the absorbent core of the present invention that has achieved wide acceptance and commercial success is described in U.S. Pat. No. 4,950,264 entitled "Thin, Flexible Sanitary Napkin" issued to Osborn III on Aug. 21, 1990. A preferred embodiment of the absorbent core has a generally rectangular shape with rounded ends such as shown in FIG. 1 (i.e., linear core side edges 56 and arcuate core end edges 58). The absorbent core 28 may be formed from comminuted wood pulp fibers, and/or airfelt; that is profiled in the lateral direction and the longitudinal direction to be thicker in the central region of the absorbent core for improved absorbency and fit of the product.

The backsheet 26 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the body discharges such as menses absorbed and contained in the absorbent core 28 from wetting articles which contact the sanitary napkin such as pants, pajamas and undergarments. The backsheet may thus include a woven or nonwoven material, polymeric films such as thermoplastic films of polyethylene or polypropylene, or composite materials such as a film-coated nonwoven material. The backsheet 26 may have vapor permeability. Preferably, the backsheet is a polyethylene film having a thickness of from about 0.012 mm (0.5 mil) to about 0.051 mm (2.0 mils). An exemplary polyethylene film is manufactured by Clopay Corporation of Cincinnati, Ohio. The size of the backsheet is dictated by the size of the absorbent core and the exact sanitary napkin design selected. In a preferred embodiment, the backsheet extends beyond the absorbent core a minimum distance around the entire sanitary napkin periphery.

The topsheet 24 is compliant, soft feeling, and non-irritating to the wearer's skin. Further, the topsheet 24 is liquid pervious permitting liquids (e.g., menses and/or urine) to readily penetrate through its thickness. For the present invention, a preferred topsheet is formed by an apertured plastic film. Apertured plastic films, formed films, are preferred for the topsheet because they are pervious to such body discharges and yet non-absorbent. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane and Smith on Apr. 13, 1982; U.S. Pat. No. 4,342,314 entitled "Resilient Plastic Web Exhibiting Fiber-Like Properties", which issued to Radel and Thompson on Aug. 3, 1982; and U.S. Pat. No. 4,463,045 entitled "Macroscopically Expanded Three-Dimensional Plastic Web Exhibiting Non-Glossy Visible Surface and Cloth-Like Tactile Impression", which issued to Ahr, Lewis, Mullane, and Ouellette on Jul. 31, 1984. The preferred topsheet for the present invention is the formed film described in one or more of the above patents and marketed on sanitary napkins by The Procter & Gamble Company as "DRI-WEAVE". Alternatively, the topsheet may be manufactured from a wide range of materials, such as porous foams; reticulated foams; or woven or nonwoven webs of natural fibers (e.g., wood or cotton fibers), synthetic fibers (e.g., polyester or polypropylene fibers), or combinations of natural and synthetic fibers. In a preferred embodiment of the present invention, the body surface 25 of the formed film topsheet is hydrophilic. The hydrophilic body surface helps liquid to transfer through the topsheet faster than if the body surface 25 was not hydrophilic. This diminishes the likelihood that menstrual fluid will flow off the topsheet rather than being absorbed by the absorbent core. In a preferred embodiment, surfactant is incorporated into the polymeric materials of the formed film topsheet. A formed film topsheet with surfactant incorporated therein is described in PCT publication WO93/09741 published on May 27, 1993. Alternatively, the body surface 25 of the topsheet can be made hydrophilic by treating it with a surfactant. The surfactant would preferably be substantially evenly and completely distributed throughout the body surface 25 of the topsheet. This can be accomplished by any of the common techniques well-known to those skilled in the art. For example, the surfactant can be applied to the topsheet by spraying, by padding, or by use of transfer rolls.

Referring to FIG. 1, the sanitary napkin 20 has channels 36. Herein, "channel" refers to a generally elongated depression formed in at least a portion of an absorbent article. The channel can be formed by, e.g., reducing the amount of the absorbent core at the channel portion, and/or compressing or embossing the absorbent core at the channel portion to densify there. By these operations, the portion of the absorbent article at the channel is formed into a generally elongated depression. The channel tends to preferentially diffuse body fluid and lets body fluid flow along the direction in which the channel extends. Therefore, the channel is useful to control body fluid flow, e.g., to reduce lateral leakage of body fluid by disposing the channel in an appropriate position of an absorbent aticle. The channel also works as a preferential bending axis of the absorbent article. Therefore, the absorbent article bends at the channel, e.g., to provide a better fit of the absorbent article to the wearer's body.

The sanitary napkin 20 has a pair of the channel 36 extending generally along the longitudinal side edges 30 of the sanitary napkin 20 and being disposed at a transversely spaced interval. Each of the channels 36 has an arcuate shape curving toward the longitudinal centerline L of the sanitary napkin 20. A pair of the channels 36 has the narrowest interval between themselves at the center of the longitudinal direction of the sanitary napkin 20. Alternatively, the channel may have any configuration, e.g., one or more straight line-like. shape extending along the longitudinal centerline L, one or more curved shape generally along the longitudinal centerline L, an oval shape, a rectangle shape, a triangle shape, a polygonal shape, or any other shape. Further, the sanitary napkin 20 may have a channel extending transversely.

In the embodiment shown in FIG. 1, the lateral interval of the channels 36 is variable. The lateral interval of the channels 36 is preferably wide enough to provide a sufficient area between the channels 36 such that the body fluid hits there. The interval of the channels 36 is at least 25 mm, preferably at least 30 mm, more preferably at least 36 mm. The length of the channel 36 is also variable. The length of the channel 36 should be determined in relation to the length of the absorbent core 28. The edge 38 of the channel 36 is preferably situated away from the core end edge 58 by at least 2 mm, preferably at least 4 mm, more preferably at least 6 mm. This prevents the channel 36 from extending into the periphery 34 of the sanitary napkin 20 even if the position of the channel 36 is shifted due to machine tolerance. The length of the channel 36 is between 10% and 98%, preferably between 20% and 90%, more preferably between 25% and 85%, of the length of the absorbent core in the longitudinal direction.

Figure 4:
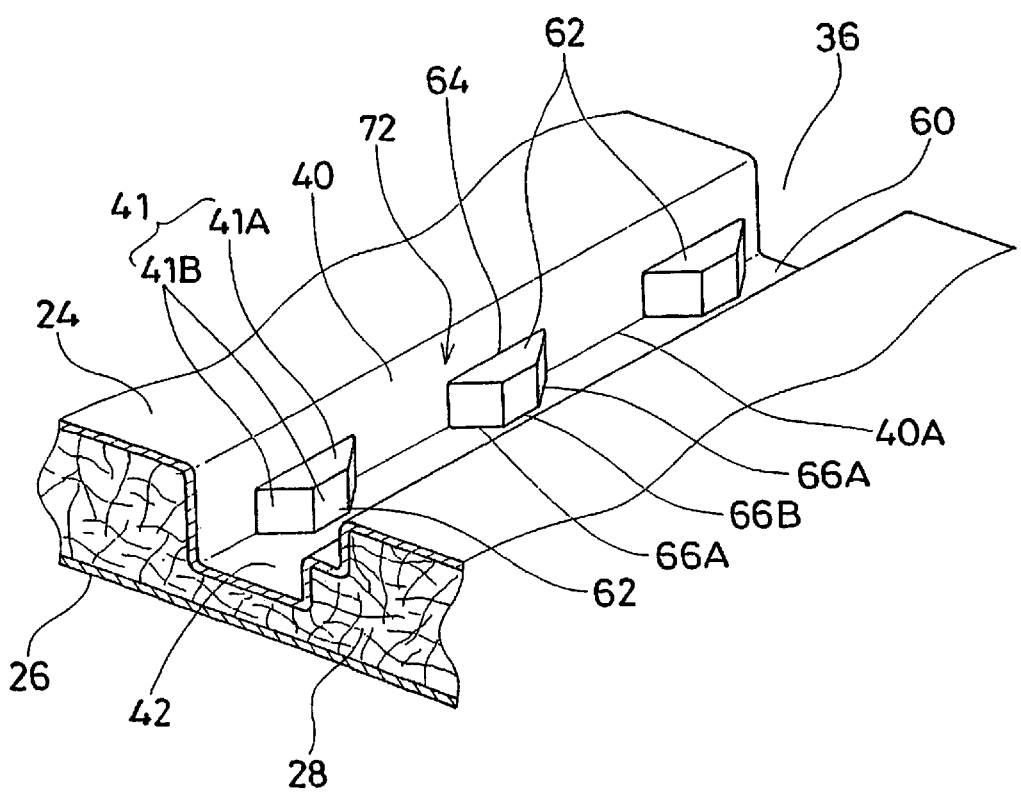
FIG. 4 is a fragmentary perspective view of the channel shown in FIG. 1.

The channel 36 is formed by compressing the topsheet 24 and the absorbent core 28 toward the backsheet 26. The topsheet 24 at the channel 36 is pressed into the absorbent core 28 and the absorbent core 28 is densified. As a result of compression, the channel 36 is formed to have an elongated depression such as a modified gutter-like shape having a channel wall surface 40, a channel bottom surface 42, and a ridge surface 41 as shown in FIGS. 2 and 4. In the embodiment shown in FIG. 2, the lateral width A of the channel 36 at the top surface of the topsheet 24 is between 3 mm and 5 mm, preferably between 3 mm and 4 mm, more preferably between 3 mm and 3.5 mm. The height B of the channel between the top surface of the topsheet 24 and the bottom surface 42 is between 2 mm and 7 mm, preferably between 4 mm and 6 mm, more preferably between 4 mm and 5 mm.

The channel 36 is formed to include at least one first portion 60 and at least one second portion 62 being of different compression relative to one another. In an embodiment, the first portion 60 is a portion of higher compression, and the second portion 62 is a portion of lower compression. Alternatively, the first portion 60 may be a portion of lower compression, and the second portion 62 may be a portion of higher compression. The absorbent core 28 is more compressed at the portion of higher compression 60 than at the portion of lower compression 62. In the embodiment shown in FIGS. 2 and 4, the portion of higher compression 60 is that portion compressed to form the bottom surface 42 of the channel 36. The absorbent core 28 at the portion of higher compression 60 is densified as a result of compression, and therefore has higher wicking effect than the rest of the absorbent core 28 which is less compressed or not compressed. The portion of lower compression 62 is that portion compressed but not to the extent of the portion of higher compression 60.

The channel 36 has the wall surface 40 (or wall), the bottom surface 42 and the ridge surface 41. The topsheet 24 is adhered by an adhesive 70 to the absorbent core 28 throughout the wall surface 40 (or wall), the bottom surface 42 and the ridge surface 41 of the channel 36. Herein, "bottom surface" refers to the surface of the portion of the channel formed by being compressed at the highest pressure. Herein "ridge surface" refers to the surface of the portion of the channel formed by being compressed by lower pressure than the highest pressure. Herein, "wall surface" refers to the rest of surface of the channel other than "bottom surface" and "ridge surface". Herein, "channel surface" refers to the surface including the "bottom surface", the "wall surface" and the "ridge. surface". In the embodiment shown in FIG. 4, the bottom surface 42 includes the surface of the portion of higher compression 60. The ridge surface 41 includes the upper surface 41A and the side surface 41B of the portion of lower compression 62. The wall surface 40 includes the generally vertical surface of the channel 36. The channel surface 72 includes all of these surfaces.

The channel 36 shown in FIG. 4 has more surface area than the channel which is formed only by a portion of unitary compression. The portion of lower compression 62 provides the ridge surface 41. The combination of the portions of higher and lower compression 60 and 62 imparts unevenness to the channel surface 72 and increases the area of the channel surface 72. This results in increasing the contact area between the topsheet 24 and the absorbent core 28 where the adhesive intervenes. By increasing the adhesive area, the bonding strength between the topsheet 24 and the absorbent core 28 is enhanced. Generally as unevenness increases, the surface area of the channel 36 is extended. In order to impart further unevenness to the channel surface 36, the channel 36 may further include a third portion being of different compression from the first portion and the second portion.

If an absorbent article has an additional layer between the topsheet and the absorbent core at the channel, it is preferable that the adhesive is applied both between the topsheet and the additional layer and between the additional layer and the absorbent core. Alternatively, the topsheet and the additional layer may be joined by any means known to those skilled in the art, such as heat, heat and pressure, ultrasonic, etc.

Figure 3:
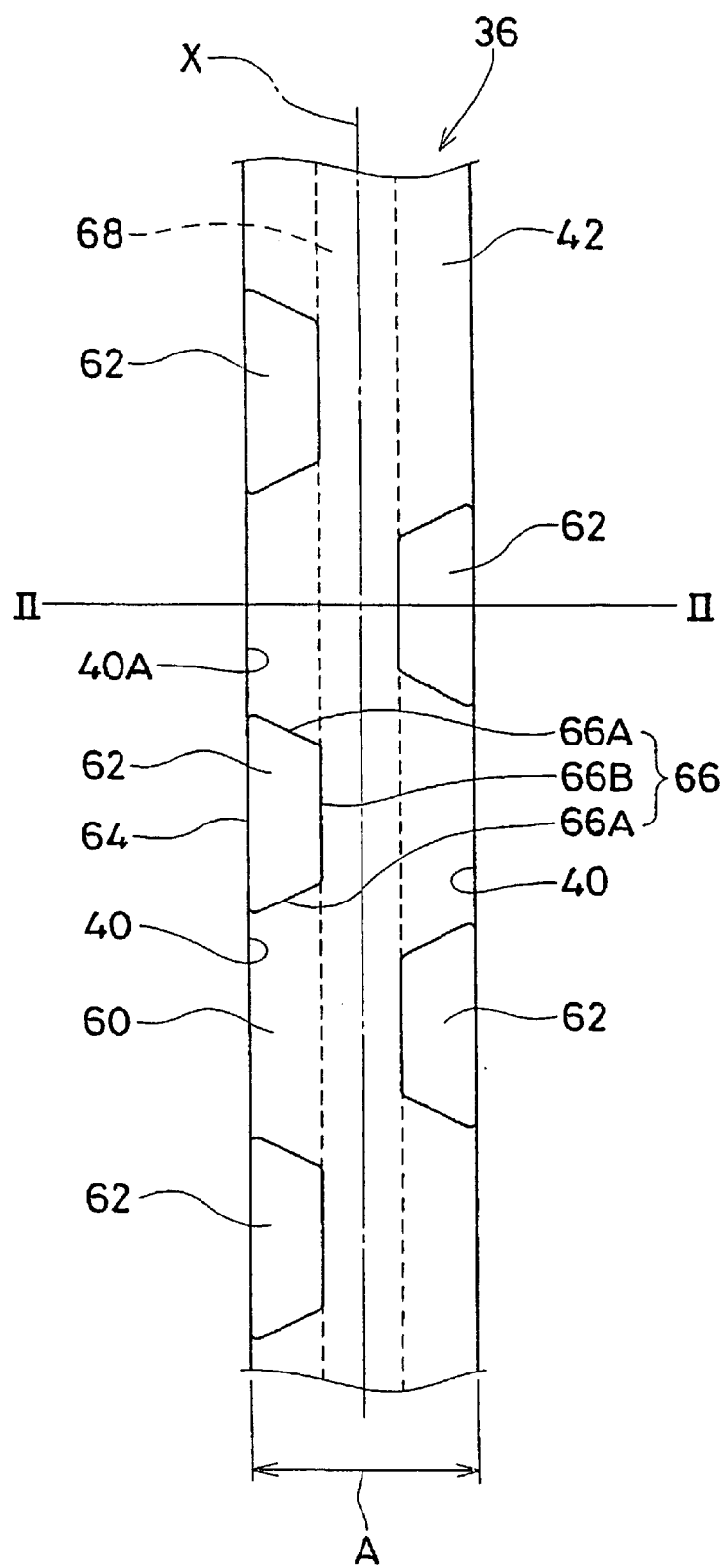
FIG. 3 is a top plan view of an embodiment of the channel shown in FIG. 1.

In the embodiment shown in FIG. 3, the portion of lower compression 62 has a generally trapezoid shape encompassed by a base edge 64, and three generally linear boundaries 66 (including a pair of side boundaries 66A and a distal boundary 66B) when the portion of lower compression 62 is viewed from the top. The base edge 64 is the portion where the upper surface 41A of the ridge surface 41 intersects with the wall surface 40 (refer to FIG. 4). The boundary 66 is the portion where the side surfaces 41A and 41B of the ridge surface 41 intersect with the bottom surface 42. The portion of higher compression 60 is encompassed by the side boundaries 66A, the distal boundary 66B and a wall base edge 40A when the portion of higher compression 60 is viewed from the top. The wall base edge 40A is the portion where the bottom surface 42 intersects with the wall surface 40. The distal boundary 66B projects from the wall 40 toward the longitudinal centerline X of the channel 36, however does not project beyond the longitudinal centerline X. Herein, "longitudinal centerline" of the channel means a line which generally bisects the channel width between the opposite walls 40 of the channel 36. Therefore, if the channel is curved, the longitudinal centerline X is also curved generally along the opposite walls 40 of the channel 36.

The portion of higher compression 60 extends continuously in the direction along which the channel 36 extends. The portion of lower compression 62 is disposed so as not to terminate continuity of the portion of higher compression 60 in the direction along which the channel extends. Herein, "continuously", "continuous", or "continuity" refers to a configuration where a portion of the channel has a generally even geometry at least in the portion of the channel without having substantial aberration. When the "continuity" of the portion of higher compression 60 terminates, the geometry of the channel 36 alters across the width of the channel 36, e.g., from the portion of higher compression 60 to the portion of lower compression 62. As shown in FIG. 4, the portion of higher compression 60 forms the bottom surface 42 of the channel 36 which has a generally even geometry (i.e., generally even surface). The portion of higher compression 60 extends continuously along at least 30%, preferably at least 40%, more preferably at least 50%, of the length of the channel 36. In the embodiment shown in FIG. 1, the portion of higher compression 60 extends continuously along the entire length of the channel 36. The portion of higher compression 60 extending continuously along the channel 36 provides a continuously even bottom surface and a continuous high density portion in the direction in which the channel 36 extends.

A plurality of the portions of lower compression 62 are disposed at spaced intervals from one another as shown in FIGS. 3 and 4. The intervals can be consistent, variable in distance and/or relative orientation. The portions of lower compression 62 are arranged along two opposite walls 40 of the channel 36. None of the portions of lower compression 62 is disposed across the width of the channel between the opposite walls 40, therefore none of the portions of lower compression 62 terminates the continuity of the higher compression 60 in the direction in which the channel 36 extends.

In addition, because none of the portions of lower compression 62 projects beyond the longitudinal centerline X, the portion of higher compression 60 has a linear portion of higher compression 68 along the longitudinal centerline X. In FIG. 3, the linear portion of higher compression 68 is shown by the region encompassed by the dotted lines and the distal boundaries 66B of the portions of lower compression 62. The linear portion of higher compression 68 extending continuously along the channel 36 forms a continuously even linear bottom surface. Herein, "linear portion" means a portion of higher compression extending in generally the same direction as the channel, while maintaining a generally constant width. Therefore, if the channel is straight linear, the linear portion of higher compression is also straight linear. If the channel is curvilinear, the linear portion of higher compression is also curvilinear.

The portion of higher compression 60 provides a preferential path for fluid flow. Because the portion of higher compression 60 has the continuously even bottom surface, it allows body fluid to flow smoothly along it. Once the body fluid is drawn to the continuous high density portion, the continuous high density portion preferentially diffuses body fluid along the length of the portion of higher compression 60. The channel 36 also has the portion of lower compression 62 to limit the area of the portion of higher compression 60 (i.e., the area of even bottom surface) in the channel 36 without terminating the continuity of the portion of higher compression 60. Therefore, the presence of the portion of lower compression prevents the body fluid from flowing too quickly along the channel 36. Thus, the portion of higher compression 60 extending continuously along the channel 36 and the portion of lower compression 62 enables a controlling of fluid flow (i.e., controlled speed, but smooth flow) along the channel 36.

In the embodiment shown in FIGS. 3 and 4, there is a boundary between the portion of higher compression 60 and the lower compression 62 as explained. Herein, "boundary" refers to a portion where the geometry of the channel 36 alters from a first portion to a second portion with substantial aberration (e.g., from the portion of higher compression 60 to the portion of lower compression 62). The two side boundaries 66A are disposed at an angle with respect to the longitudinal centerline X of channel 36 and across the width of the channel 36. In addition, the two side boundaries 66A and the distal boundary 66B are disposed generally linear and generally non-parallel to one another.

The portion of higher compression 60 provides a stronger joining between the topsheet 24 and the absorbent core 28 than the portion of lower compression 62. Therefore, when peeling force is applied, the portion of higher compression 60 is more capable of resisting the peeling force than the portion of lower compression 62. The peeling force can be caused by twisting of the sanitary napkin 20 during use, such as during walking or posture change. Such peeling force caused by twisting of the sanitary napkin 20 tends to be applied to the channel 36 generally diagonally in two different directions D1 and D2 (refer to FIG. 1) (Although FIG. 1 shows only two forces in different directions D1 and D2, these are not all the directional forces applied to the sanitary napkin 20. There are various other potential directional forces. For the purposes of this description, only two forces in the directions D1 and D2 are described because they are the directions where the force will more likely occur.). The force in the direction D1 usually occurs when the sanitary napkin 20 twists in the direction T and the force in the direction D2 usually occurs when the sanitary napkin 20 twists in the direction S. The linear boundaries 66 of the portion of higher compression 60 extending in different directions (i.e., non-parallel) in the embodiment shown in FIG. 3 are capable of resisting peeling force at least in these two directions. The linear shape of the boundary 51 is believed a shape more likely to resist the force applied.

FIGS. 5–11 show some of alternative embodiments of the sanitary napkin shown in FIGS. 1–4. It should be noted that other alternative embodiments other than the below are also possible.

Figure 5:
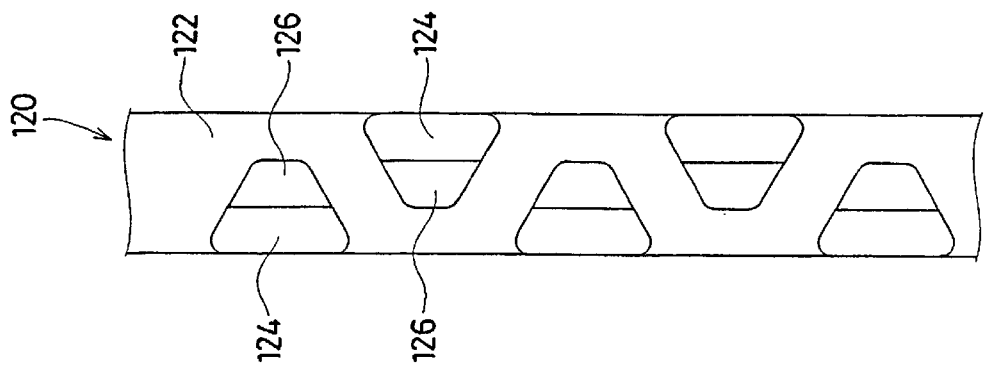
FIG. 5 is a top plan view of another alternative embodiment of the channel shown in FIG. 1.

FIG. 5 shows an alternative embodiment of the channel. The channel 100 includes at least one first portion 102 and at least one second portion 104 being of different compression relative to one another. In the embodiment, the first portion 102 is a portion of higher compression, and the second portion 104 is a portion of lower compression. The portion of lower compression 104 has a generally trapezoid shape including a base edge 106 and a distal edge 108 when the portion of lower compression 104 is viewed from the top. In this embodiment, the distal edge 108 projects beyond the longitudinal centerline X. Therefore, the channel 100 shown in FIG. 5 does not have a linear portion of higher compression. However, the portion of higher compression 102 extends continuously circuitously along the channel 100. Herein, "circuitously" encompasses any configuration which is not straight such as winding, sinusoidal, or zigzag configuration.

Figure 6:
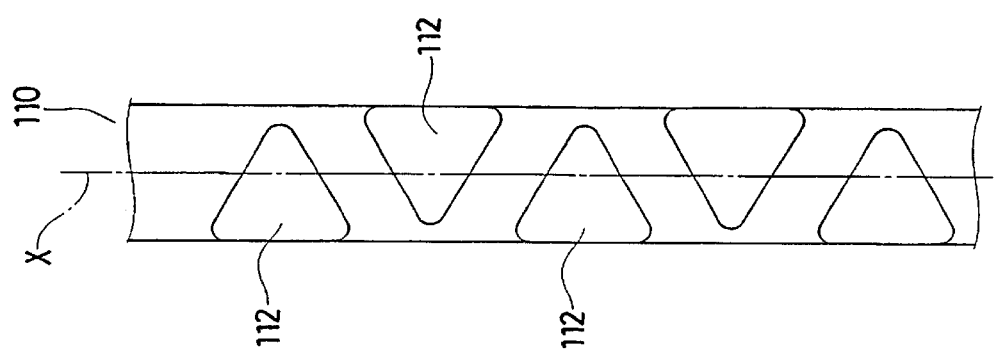
FIG. 6 is a top plan view of another alternative embodiment of the channel shown in FIG. 1.

FIG. 6 shows another alternative embodiment of the channel. In this embodiment, the portion of higher compression 112 of the channel 110 has a triangle shape with a round apex. Alternatively, the portion of higher compression 112 may have a triangle shape with a sharp apex. The embodiments shown in FIGS. 5 and 6 provides more geometrical change to the channel surface than the embodiment shown in FIGS. 2–4. Therefore, the area where the adhesive is applied between the topsheet 24 and the absorbent core 28 increases.

Figure 7:
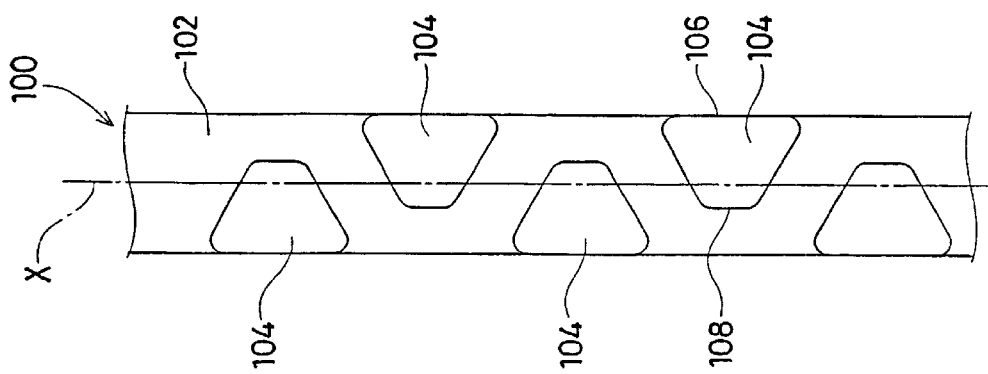
FIG. 7 is a top plan view of another alternative embodiment of the channel shown in FIG.1.
Figure 8:
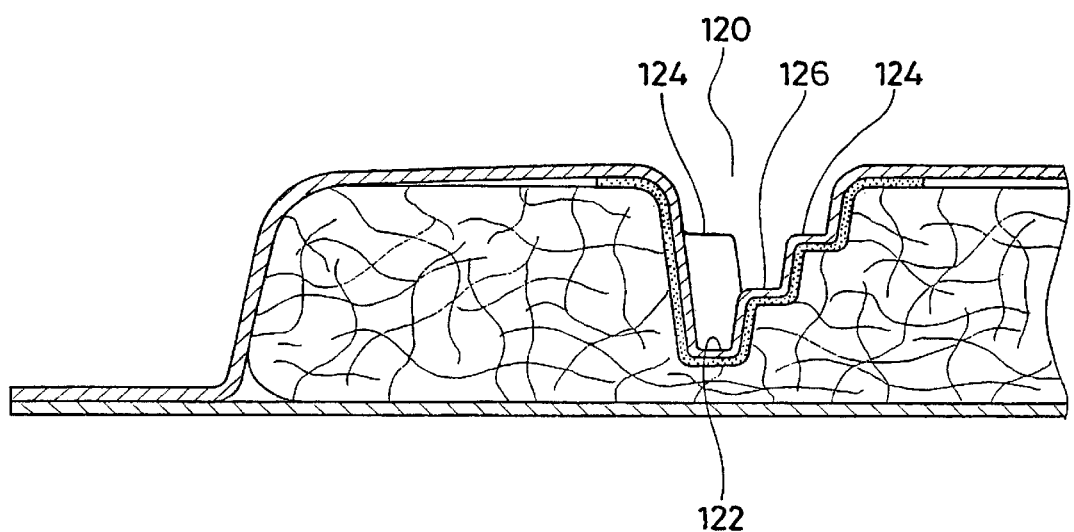
FIG. 8 is a fragmentary cross-sectional view of the absorbent article having the channel shown in FIG. 7.

FIGS. 7 and 8 show another alternative embodiment of the channel. In this embodiment, the channel 120 includes at least one first portion 122, at least one second portion 124, and at least one third portion 126 being of different compression relative to each other. In the embodiment, the first portion 122 is a portion of higher compression, the second portion 124 is a portion of lower compression, and the third portion 126 is a portion of middle compression between higher compression and lower compression. The overall shape of the portion of higher compression 122 is the generally same as that of the portion of higher compression 102 shown in FIG. 5 when it is viewed from the top. This embodiment provides more geometrical change to the channel surface than the embodiment shown in FIG. 5 because of the presence of the portion of middle compression 126 as well as the portion of lower compression 128. Further, the channel may have four or more portions being different compression relative to each other.

Figure 9:
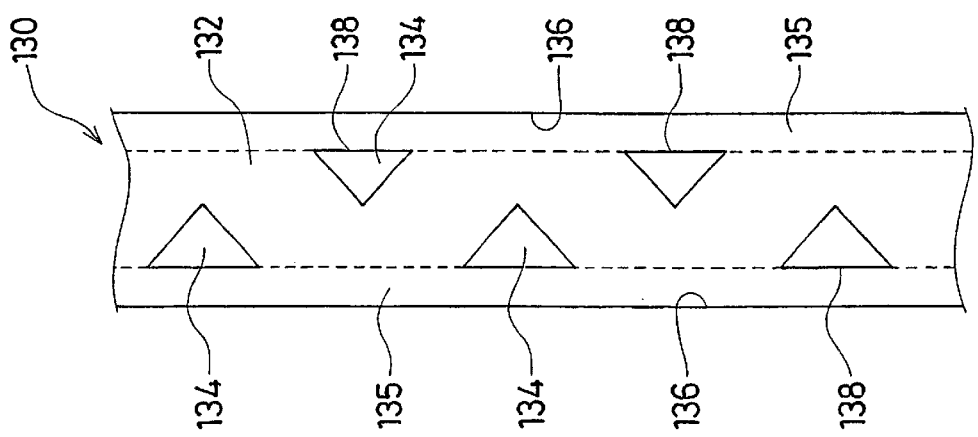
FIG. 9 is a top plan view of another alternative embodiment of the channel shown in FIG. 1.

FIG. 9 shows another alternative embodiment of the channel. In this embodiment, the channel 130 includes at least one first portion 132 and at least one second portion 134 being of different compression relative to one another. In the embodiment, the first portion 132 is a portion of higher compression, and the second portion 134 is a portion of lower compression. The portion of lower compression 134 has a triangle shape. The portion of lower compression 134 is apart from the opposite walls 136 of the channel 130. The channel 130 has two linear portions of higher compression 135 along the opposite walls 136. In FIG. 9, the linear portions of higher compression 135 are shown by the region encompassed by the wall 136, the dotted line and the base edge 138 of the portions of lower compression 62. The channel 130 may have three or more linear portions of higher compression.

Figure 10:
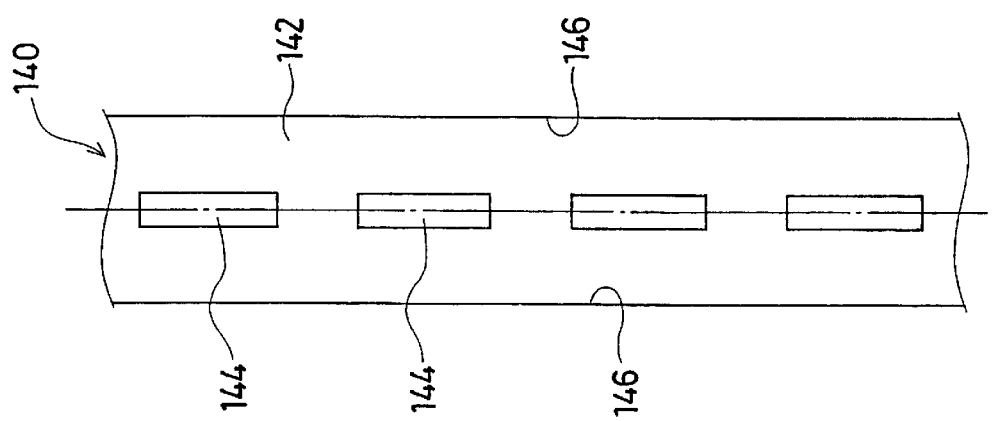
FIG. 10 is a top plan view of another alternative embodiment of the channel shown in FIG. 1.

FIG. 10 shows another alternative embodiment of the channel. In this embodiment, the channel 140 includes at least one first portion 142 and at least one second portion 144 being of different compression relative to one another. In the embodiment, the first portion 142 is a portion of higher compression, and the second portion 144 is a portion of lower compression. The portion of lower compression 144 has a rectangle shape. Each of the portions of lower compression 144 are disposed along the longitudinal centerline X, and is apart from the opposite walls 146. The channel 140 has two linear portions of higher compression along the opposite walls 136.

Figure 11:
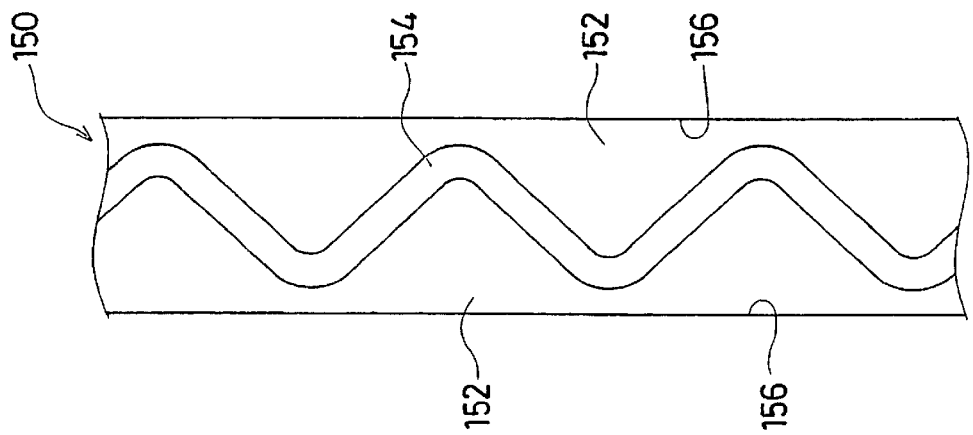
FIG. 11 is a top plan view of another alternative embodiment of the channel shown in FIG. 1.

FIG. 11 shows another alternative embodiment of the channel. In this embodiment, the channel 150 includes at least one first portion 152 and at least one second portion 154 being of different compression relative to one another. In the embodiment, the first portion 152 is a portion of higher compression, and the second portion 154 is a portion of lower compression. The portion of lower compression 154 extends circuitously along the channel 150 without touching the opposite walls 156 of the channel 150. There are two portions of higher compression 152 on both sides of the portion of lower compression 154, which are disposed at laterally spaced interval.

Figure 12:
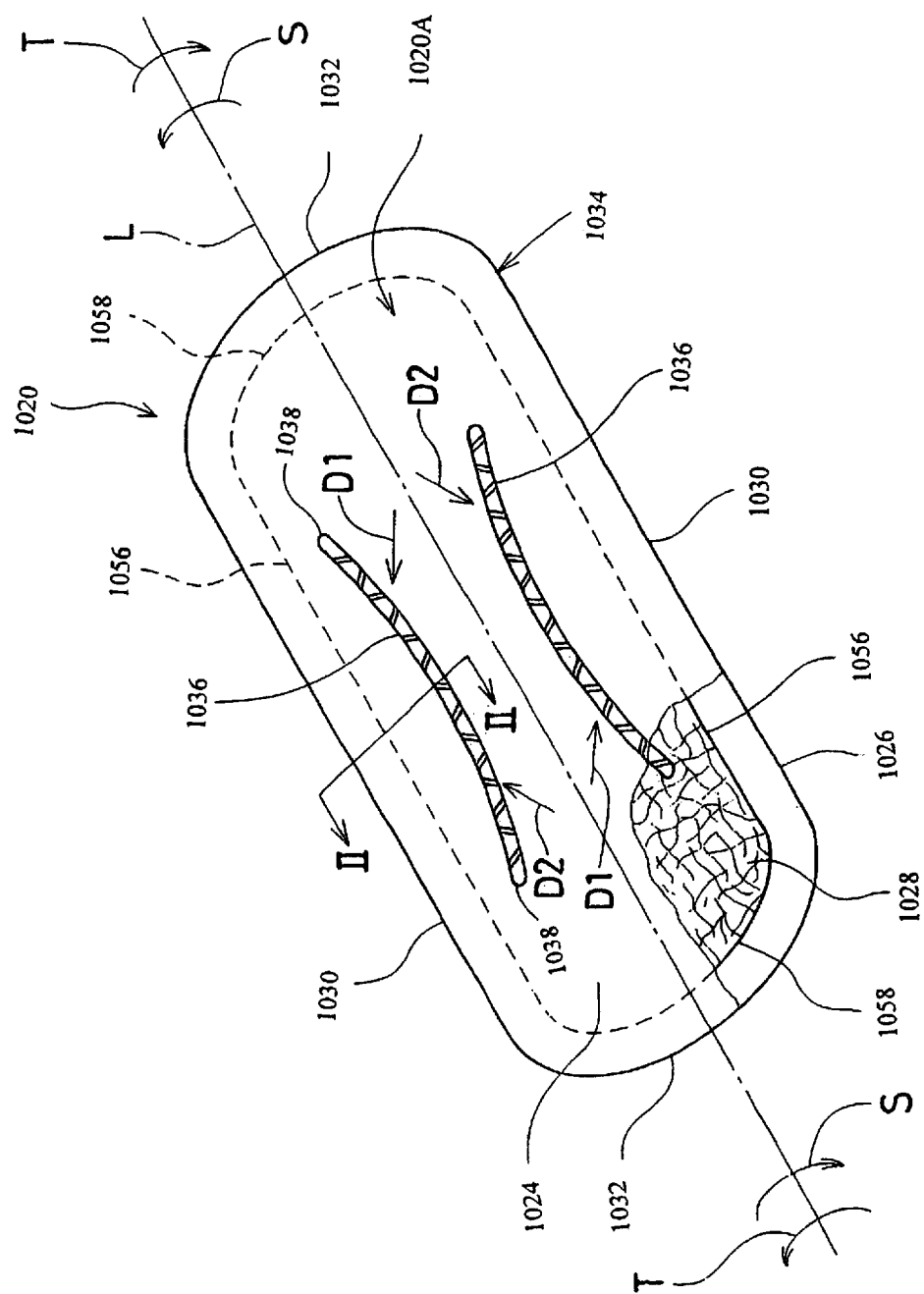
FIG. 12 is a perspective view of another alternative embodiment of the absorbent article of the present invention with a portion of the structure being cut-away to more clearly show the construction of the absorbent article.

FIGS. 12–15 show an alternative embodiment of the sanitary napkin of the present invention. FIG. 12 is a perspective view of the absorbent article of alternative embodiment of the present invention with a portion of the structure being cut-away to more clearly show the construction of the sanitary napkin 1020. As shown in FIG. 12, the sanitary napkin 1020 has two centerlines, a principal longitudinal centerline L and a principal transverse centerline (not shown in FIGS). The sanitary napkin 1020 also has two spaced apart longitudinal side edges 1030, two spaced apart transverse or end edges (or "ends") 1032, which together form the periphery 1034 of the sanitary napkin 1020.

The sanitary napkin 1020 basically includes two surfaces, a liquid pervious body-contacting surface or "body surface" 1020A that is intended to be worn adjacent to the body of the wearer, and a liquid impervious garment surface 1020B (not shown in FIG. 1). The body surface 1020A includes a liquid permeable topsheet 1024 and the liquid impermeable garment surface 1020B includes a liquid impermeable backsheet 1026 which is joined to the topsheet 1024. The sanitary napkin 1020 includes an absorbent core 1028 interposed between the topsheet 1024 and the backsheet 1026. The sanitary napkin 1020 further includes channels 1036 on the body surface 1020A.

Figure 13:
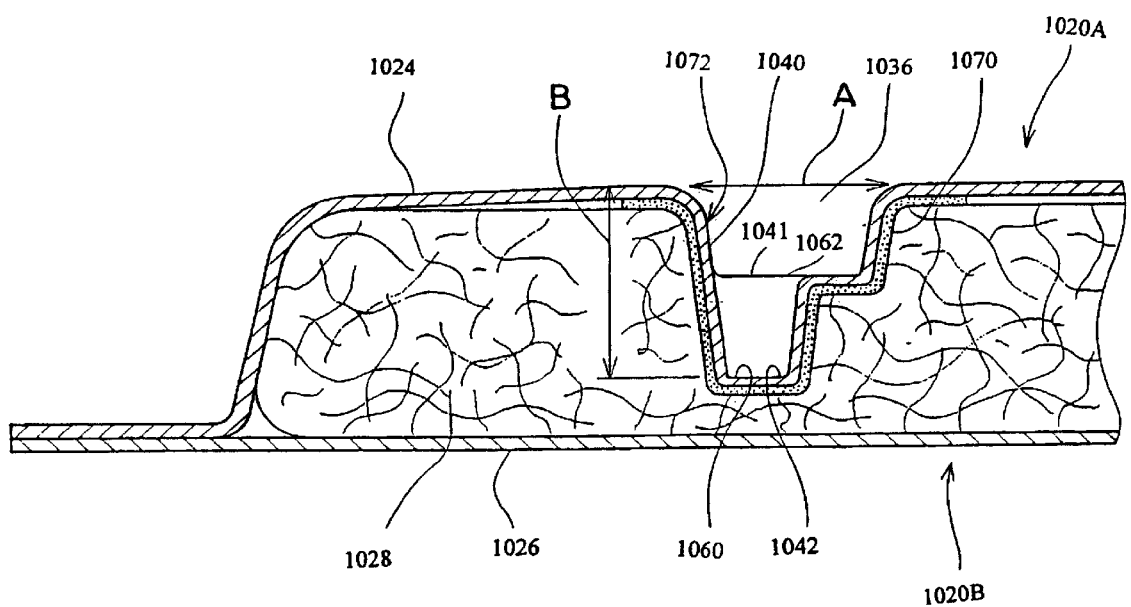
FIG. 13 is a fragmentary cross-sectional view of the absorbent article taken along the line II—II of FIG. 12.

FIG. 13 shows the individual components of the sanitary napkin 1020. The sanitary napkin 1020 has at least three primary components, the topsheet 1024, the backsheet 1026, and the absorbent core 1028 interposed therebetween. The topsheet 1024, the backsheet 1026, and the absorbent core 1028 may have dimensions as described above and may be assembled in a manner as described above. The absorbent core 1028, the topsheet 1024, and the backsheet 1026 may be formed by the materials described above.

Referring to FIG. 12, the sanitary napkin 1020 has a pair of the channel 1036 extending generally along the longitudinal side edges 1030 of the sanitary napkin 1020 and being disposed at a transversely spaced interval. Each of the channels 1036 has an arcuate shape curving toward the longitudinal centerline L of the sanitary napkin 1020. A pair of the channels 1036 has the narrowest interval between themselves at the center of the longitudinal direction of the sanitary napkin 1020. Alternatively, the channel may have any configuration as described above.

In the embodiment shown in FIG. 12, the lateral interval of the channels 1036 is variable. The lateral interval of the channels 1036 is preferably wide enough to provide a sufficient area between the channels 36 such that the body fluid hits there. The interval of the channels 1036 is at least 25 mm, preferably at least 30 mm, more preferably at least 36 mm. The length of the channel 1036 is also variable. The length of the channel 1036 should be determined in relation to the length of the absorbent core 1028. The edge 1038 of the channel 1036 is preferably situated away from the core end edge 1058 by at least 2 mm, preferably at least 4 mm, more preferably at least 6 mm. This prevents the channel 1036 from extending into the periphery 1034 of the sanitary napkin 1020 even if the position of the channel 1036 is shifted due to machine tolerance. The length of the channel 1036 is between 10% and 98%, preferably between 20% and 90%, more preferably between 25% and 85%, of the length of the absorbent core in the longitudinal direction.

Figure 15:
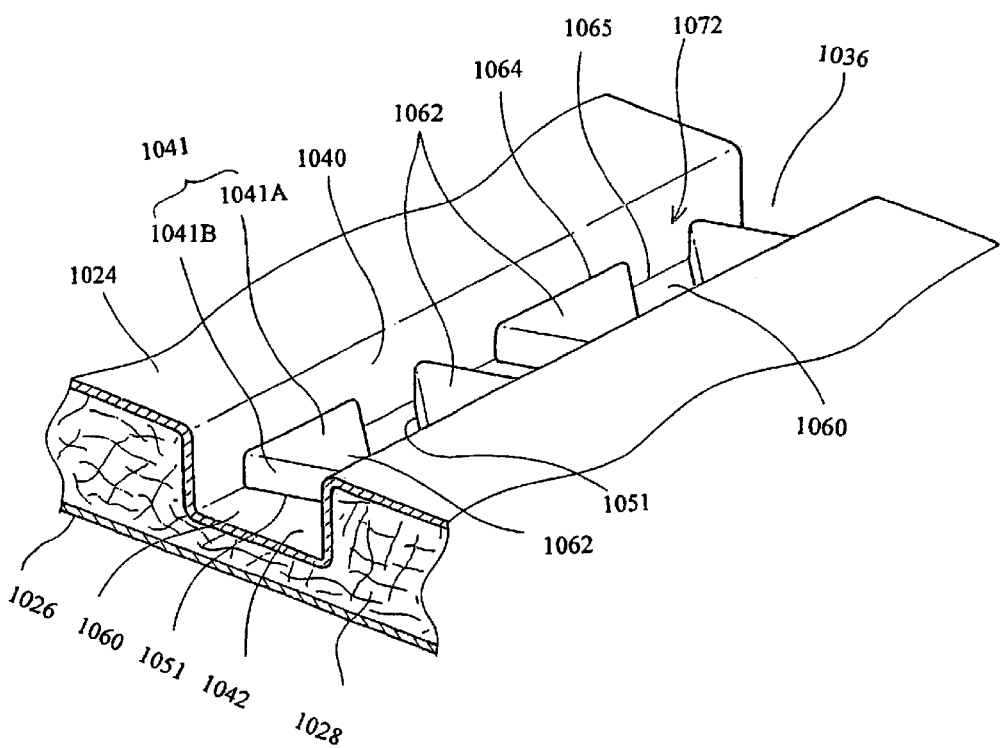
FIG. 15 is a fragmentary perspective view of the channel shown in FIG. 12.

The channel 1036 is formed by compressing the topsheet 1024 and the absorbent core 1028 toward the backsheet 1026. The topsheet 1024 at the channel 1036 is pressed into the absorbent core 1028 and the absorbent core 1028 is densified. As a result of compression, the channel 1036 is formed to have an elongated depression such as a modified gutter-like shape having a channel wall surface 1040, a channel bottom surface 1042, and a ridge surface 1041 as shown in FIGS. 13 and 15. In the embodiment shown in FIG. 13, the lateral width A of the channel 1036 at the top surface of the topsheet 1024 is between 3 mm and 5 mm, preferably between 3 mm and 4 mm, more preferably between 3 mm and 3.5 mm. The height B of the channel between the top surface of the topsheet 1024 and the bottom surface 42 is between 2 mm and 7 mm, preferably between 4 mm and 6 mm, more preferably between 4 mm and 5 mm.

The channel 1036 is formed to include at least one first portion 1060 and at least one second portion 1062 being of different compression relative to one another. In an embodiment, the first portion 1060 is a portion of higher compression, and the second portion 1062 is a portion of lower compression. Alternatively, the first portion 1060 may be a portion of lower compression, and the second portion 1062 may be a portion of higher compression. The absorbent core 1028 is more compressed at the portion of higher compression 1060 than at the portion of lower compression 1062. In the embodiment shown in FIGS. 13 and 15, the portion of higher compression 1060 is that portion compressed to form the bottom surface 1042 of the channel 1036. The absorbent core 1028 at the portion of higher compression 1060 is densified as a result of compression, and therefore has higher wicking effect than the rest of the absorbent core 1028 which is less compressed or not compressed. The portion of lower compression 1062 is that portion compressed but not to the extent of the portion of higher compression 1060.

The channel 1036 has the wall surface 1040 (or wall), the bottom surface 1042 and the ridge surface 1041. The topsheet 1024 is adhered by an adhesive 1070 to the absorbent core 1028 throughout the wall surface 1040 (or wall), the bottom surface 1042 and the ridge surface 1041 of the channel 1036. In the embodiment shown in FIG. 15, the bottom surface 1042 includes the surface of the portion of higher compression 1060. The ridge surface 1041 includes the upper surface 1041A and the side surface 1041B of the portion of lower compression 1062. The wall surface 1040 includes the generally vertical surface of the channel 1036. The channel surface 1072 includes all of these surfaces.

The channel 1036 shown in FIG. 15 has more surface area than the channel which is formed only by a portion of unitary compression. The portion of lower compression 1062 provides the ridge surface 1041. The combination of the portions of higher and lower compression 1060 and 1062 imparts unevenness to the channel surface 1072 and increases the area of the channel surface 1072. This results in increasing the contact area between the topsheet 1024 and the absorbent core 1028 where the adhesive intervenes. By increasing the adhesive area, the bonding strength between the topsheet 1024 and the absorbent core 1028 is enhanced.

Figure 14:
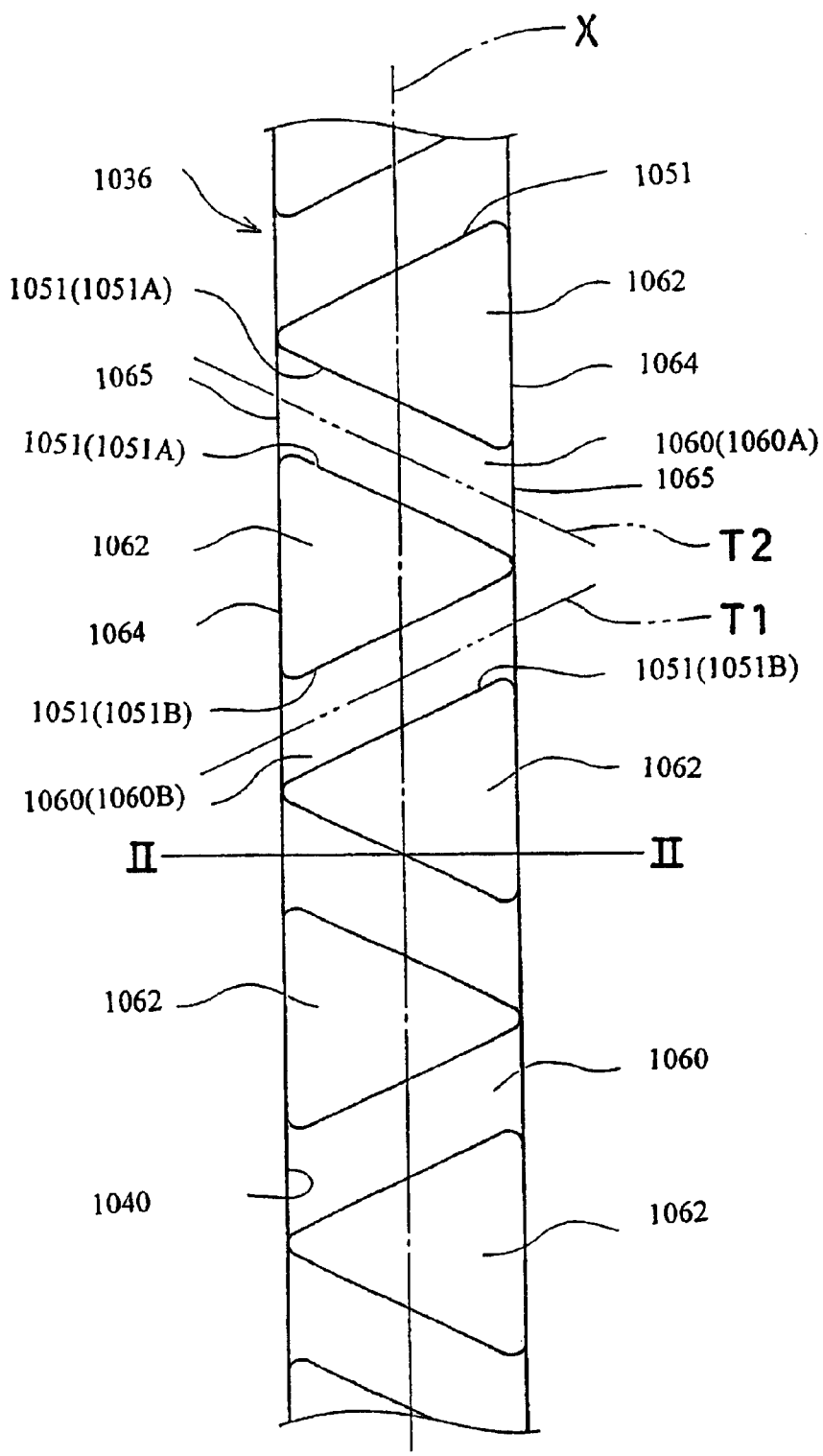
FIG. 14 is a top plan view of an embodiment of the channel shown in FIG. 12.

There is a boundary 1051 extending between the portion of the higher compression 1060 and the portion of lower compression 1062 as shown in FIGS. 14 and 15. The channel 1036 has at least two boundaries 1051 between the portion of higher compression 1060 and the portion of lower compression 1062. The two boundaries 1051 are generally linear and generally non-parallel to one another.

In the embodiment shown in FIGS. 14 and 15, the portion of higher compression 1060 and the portion of lower compression 1062 are disposed alternately in the direction of the length of the channel. Herein, "alternately" refers to a configuration where each portion of different compression terminates in the direction of the length of the channel generally across the width of the channel at the boundary and the other portion of different compression begins at the boundary. The portion of lower compression 1062 has a generally triangle shape encompassed by a base edge 1064 and two boundaries 1051 when the portion of lower compression 1062 is viewed from the top as shown in FIG. 14. The base edge 1064 is the portion where the upper surface 1041A of the ridge surface 1041 intersects with the wall surface 1040. The boundary 1051 is the portion where the side surface 1041B of the ridge surface 1041 intersects with the bottom surface 1042. The boundary 1051 is disposed at an angle with respect to the longitudinal centerline X of channel 1036 and across the width of the channel 1036. The portion of higher compression 1060 has a generally parallelogram shape encompassed by a pair of boundaries 1051 and a pair of wall base edges 1065 when the portion of higher compression 1060 is viewed from the top. The wall base edge 1065 is the portion where the bottom surface 1042 intersects with the wall surface 1040. The boundaries 1051 encompassing one portion of higher compression are generally linear and generally parallel to one another. The boundaries 1051 define an orientation of the portion of higher compression 1060. The orientation of the portion of higher compression 1060 defined by the boundaries 1051 is generally same as the orientation in which the parallel linear boundaries 1051 extend. The portions of higher compression 1060 orient in two directions T1 and T2 as shown in FIG. 14. Therefore, the boundaries 1051A of one portion of higher compression 1060A are non-parallel to the boundaries 1051B of another portion of higher compression 1060B.

The portion of higher compression 1060 provides a stronger joining between the topsheet 1024 and the absorbent core 1028 than the portion of lower compression 1062. Therefore, when peeling force exemplified by D1 and D2 in FIG. 12 is applied, the portion of higher compression 1060 is more capable of resisting the peeling force than the portion of lower compression 1062. The detail of the peeling force, such as D1 or D2, is described above. The linear boundaries 1051 of the portion of higher compression 1060 extending in two different directions (such as linear boundaries 1051A and 1051B) in the embodiment shown in FIG. 14 are capable of resisting peeling force at least in these two directions. The linear shape of the boundary 1051 is believed a shape more likely to resist the force applied.

FIGS. 16–19 show some of alternative embodiments of the sanitary napkin shown in FIGS. 12–15. It should be noted that other alternative embodiments other than the below are also possible.

Figure 16:
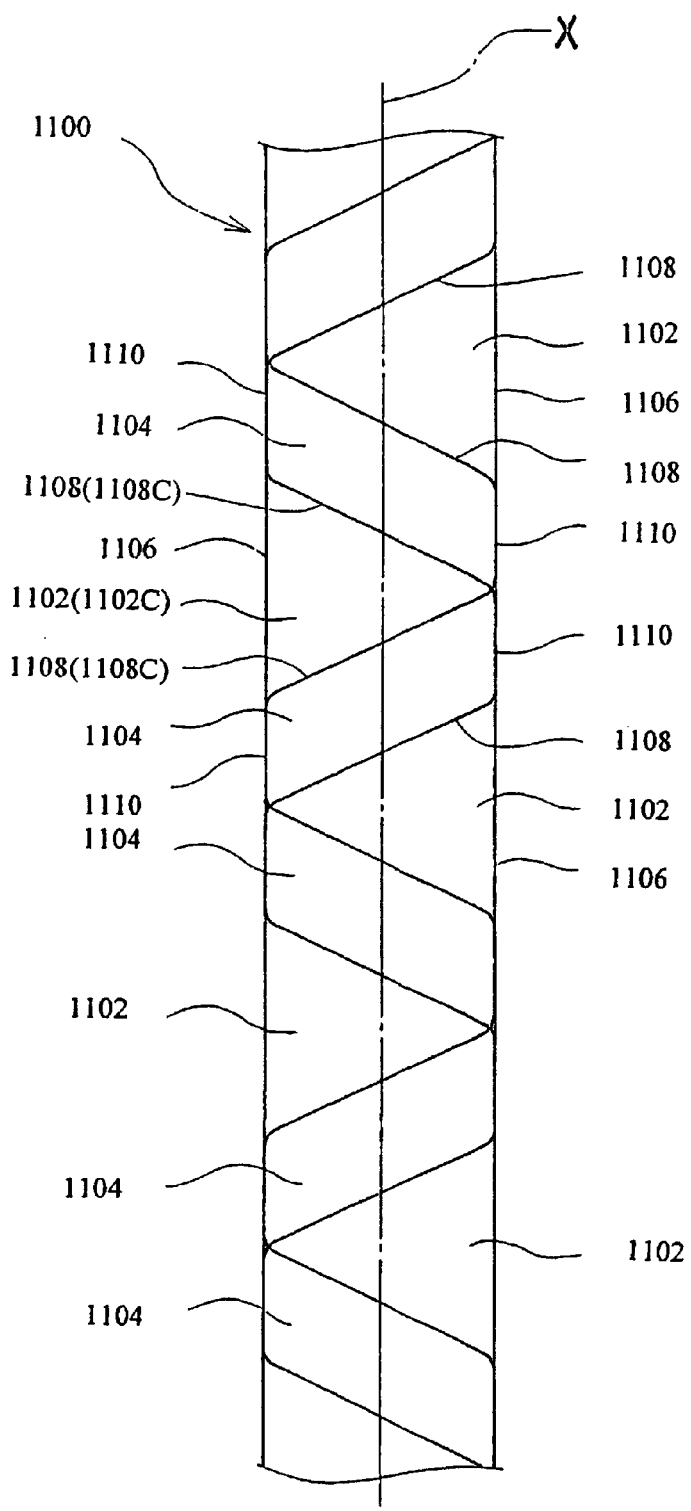
FIG. 16 is a top plan view of alternative embodiment of the channel shown in FIG. 12.
Figure 17:
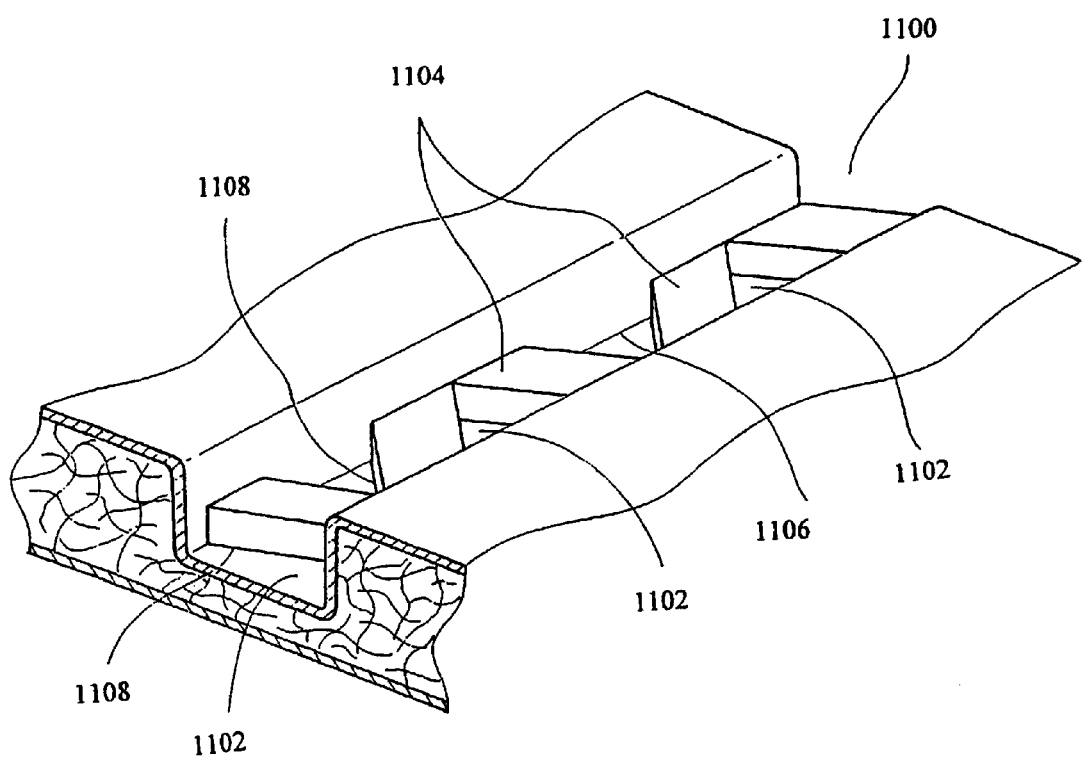
FIG. 17 is a fragmentary perspective view of the channel shown in FIG. 16.

In FIGS. 16 and 17, the channel 1100 is formed to include at least one first portion 1102 and at least one second portion 1104 being of different compression relative to one another. In the embodiment, the first portion 1102 is a portion of higher compression, and the second portion 1104 is a portion of lower compression. The portion of higher compression 1102 and the portion of lower compression 1104 are disposed alternately in the direction of the length of the channel 1100. The portion of higher compression 1102 has a generally triangle shape encompassed by a wall base edge 1106 and two boundaries 1108 when the portion of higher compression 1102 is viewed from the top. The portion of lower compression 1062 has a generally parallelogram shape encompassed by a pair of boundaries 1108 and a pair of base edges 1110 when the portion of higher compression 1160 is viewed from the top. The boundaries 1108 encompassing one portion of higher compression are generally linear and generally non-parallel to one another. In the embodiment shown in FIGS. 16 and 17, each of the portion of higher compression 1102 has non-parallel linear boundaries 1108. The linear boundaries 1108 of the portion of higher compression 1102 extending in two different directions (such as two of linear boundaries 1108C encompassing the portion of higher compression 1102C in the embodiment shown in FIG. 16) are capable of resisting peeling force at least in two directions.

Figure 18:
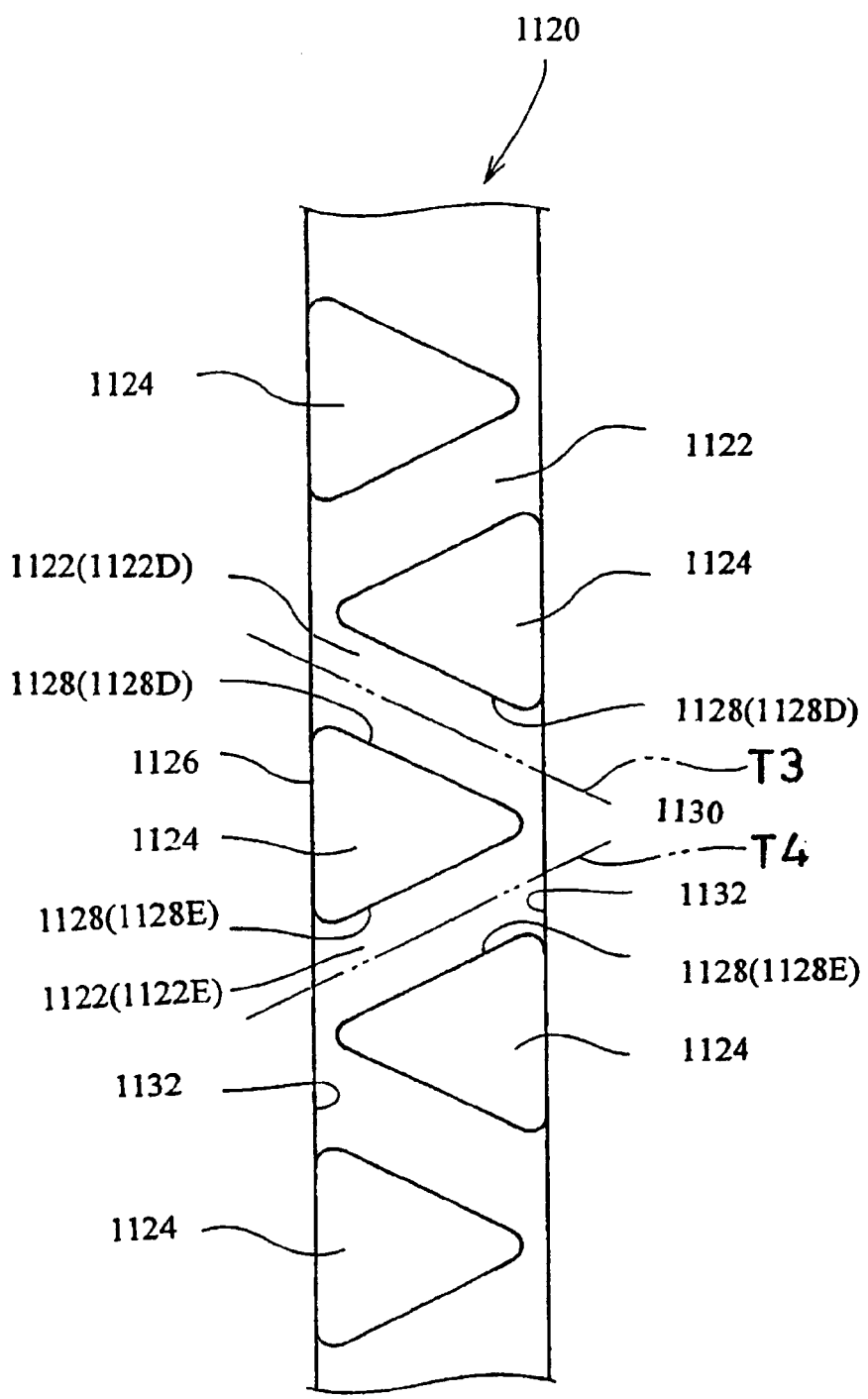
FIG. 18 is a top plan view of another alternative embodiment of the channel shown in FIG. 12.

FIG. 18 shows another alternative embodiment of the channel. The channel 1120 is formed to include at least one first portion 1122 and at least one second portion 1124 being of different compression relative to one another. In the embodiment, the first portion 1122 is a portion of higher compression, and the second portion 1124 is a portion of lower compression. Alternatively, the first portion 1122 may be a portion of lower compression and the second portion 1124 may be a portion of higher compression. The portion of lower compression 1124 has a generally triangle shape encompassed by a base edge 1126 and two boundaries 1128 when the portion of lower compression 1124 is viewed from the top. However, the apex 1130 of the triangle shape does not extend to the wall 1132 of the channel 1120. In this embodiment shown in FIG. 18, although the base edge 1126 extends to the wall 1132, the base edge 1126 may stop short of (i.e., be apart from) the wall 1132. Alternatively, the portion of lower compression 1124 may have a trapezoid shape which does not touch on the wall 1132 of the channel 1120. The portion of lower compression 1124 is disposed so as not to terminate continuity of the portion of higher compression 1122 in the direction along the channel, and the portion of higher compression 1122 extends continuously circuitously in the direction along which the channel 1120 extends. A plurality of the portions of lower compression 1124 are disposed at spaced intervals from one another as shown in FIG. 18. The intervals can be consistent, variable in distance and/or relative orientation. The portions of lower compression 1124 are arranged along two opposite walls 1132 of the channel 1120.

The portion of higher compression 1122 is encompassed by boundaries 1128 and the wall base edge 1132. The portion of higher compression 1122 is encompassed by at least generally parallel linear boundaries 1128. Although the portion of higher compression 1122 extends continuously, it could be viewed as a shape modified from the shape of the portion of higher compression 1060 shown in FIG. 15 having a pair of boundaries being generally linear and generally parallel to one another. Therefore, the boundaries 1128 define an orientation of the portion of higher compression 1122. The orientation of the portion of higher compression 1122 defined by the boundaries 1128 is generally the same as the orientation of the parallel linear boundaries 1128 extends. The portions of higher compression 1120 orient in two directions T3 and T4 as shown in FIG. 18. When the portion of higher compression 1122D is encompassed by parallel linear boundaries 1128D, the boundaries 1128D of one portion of higher compression 1122D are non-parallel to the boundaries 1128E of another portion of higher compression 1122E.

The portion of higher compression 1122 provides a preferential path for fluid flow. Because the portion of higher compression 1122 has the continuously even bottom surface in the direction of the length of the channel 1120, it allows body fluid to flow smoothly along it. Once the body fluid is drawn to the continuous high density portion formed by the portion of higher compression 1122, the continuous high density portion preferentially diffuses body fluid along the length of the portion of higher compression 1122. The channel 1120 also has the portion of lower compression 1124 to limit the area of the portion of higher compression 1122 (i.e., the area of even bottom surface) in the channel 1120 without terminating the continuity of the portion of higher compression 1060. Therefore, the presence of the portion of lower compression 1124 prevents the body fluid from flowing too quickly along the channel 1120. Thus, the portion of higher compression 1122 extending continuously along the channel 1120 and the portion of lower compression 1124 enables a controlling of fluid flow (i.e., controlled speed, but smooth flow) along the channel 1120.

The portion of higher compression 1122 may have a linear portion of higher compression in the direction of the length of the channel 1120. The linear portion of higher compression extending continuously along the channel 1120 forms a continuously even linear bottom surface.

Figure 19:
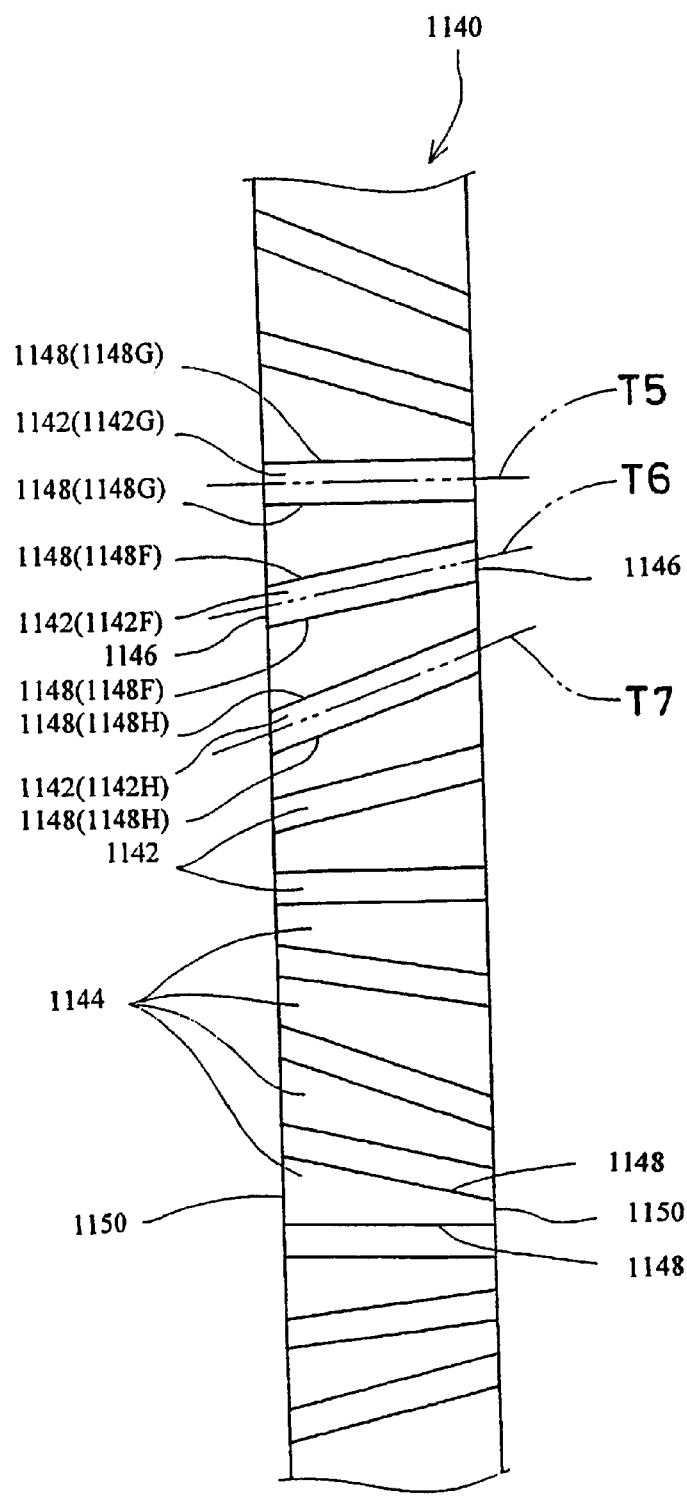
FIG. 19 is a top plan view of another alternative embodiment of the channel shown in FIG. 12.

FIG. 19 shows another alternative embodiment of the channel. The channel 1140 is formed to include at least one first portion 1142 and at least one second portion 1144 being of different compression relative to one another. In the embodiment, the first portion 1142 is a portion of higher compression, and the second portion 1144 is a portion of lower compression. Alternatively, the first portion 1142 may be a portion of lower compression and the second portion 1144 may be a portion of higher compression. The portion of higher compression 1142 and the portion of lower compression 1144 are disposed alternately in the direction of the length of the channel 1140. The portion of higher compression 1142 has a generally parallelogram shape encompassed by a pair of boundaries 1148 and a pair of wall base edges 1146 when the portion of higher compression 1142 is viewed from the top. The portion of lower compression 1144 is encompassed by a pair of boundaries 1148 and a pair of base edges 1150 when the portion of lower compression 1144 is viewed from the top.

The boundaries 1148 encompassing the portion of higher compression 1142 are generally linear and generally parallel to one another. The boundaries 1148 defines an orientation of the portion of higher compression 1142. The orientation of the portion of higher compression 1142 defined by the boundaries 1148 is generally same as the orientation of the parallel linear boundaries 1148 extends. The portions of higher compression 1142 may orient in three or more directions. In the embodiment shown in FIG. 19, the portions of higher compression 1142 orient in three different directions, T5, T6, and T7. Therefore, the boundaries 1148F of one portion of higher compression 1142F is non-parallel to the boundaries 1148G of another portion of higher compression 1142G and non-parallel to the boundaries 1148H of another portion of higher compression 1142H. Thus, the linear boundaries 1148 of the portion of higher compression 1142 extending in three or more different directions (such as linear boundaries 1148F, 1148G, and 1148H) in the embodiment shown in FIG. 19 are more capable of resisting peeing force in multiple directions.

It is to be recognized that the foregoing detailed description of the preferred embodiment of the present invention is given merely by way of illustration, and that numerous modifications and variations may become apparent to those skilled in the art without departing from the spirit and scope of the invention. Therefore, the scope of the present invention is to be determined by reference to the appended claims.

What is claimed is:

1. An absorbent article comprising a liquid permeable topsheet, a liquid impermeable backsheet, an absorbent core therebetween, and a channel, wherein the channel has a wall surface, at least one portion of higher compression and at least one portion of lower compression;

said portion of higher compression comprises a bottom surface;

said portion of lower compression comprises a ridge surface;

said ridge surface comprising a base edge, an upper surface and at least two side surfaces, said side surfaces being non-parallel to one another, and said upper surface and said wall surface intersect at said base edge.

2. The absorbent article of claim 1 wherein said channel further comprises a length and a longitudinal centerline, said longitudinal centerline extending in the direction of the length of the channel, and said side surfaces are disposed at an angle with respect to the longitudinal centerline.

3. The absorbent article of claim 1 wherein said ridge surfaces are disposed alternately in the direction of the length of said channel.

4. The absorbent article of claim 1 wherein said ridge surfaces further comprise a distal boundary that does not project beyond the longitudinal centerline.

5. The absorbent article of claim 3 wherein the ridge surfaces are a trapezoidal shape.

* * * * *